(12) United States Patent
Couchou-Meillot et al.

(10) Patent No.: US 12,099,073 B2
(45) Date of Patent: Sep. 24, 2024

(54) DEVICE FOR DETERMINING A VOLUME OF GAS IN A SAMPLE

(71) Applicant: TotalEnergies SE, Courbevoie (FR)

(72) Inventors: Gilles Couchou-Meillot, Pau (FR); Paul Pochitaloff-Huvale, Pau (FR)

(73) Assignee: TOTALENERGIES SE, Courbevoie (FR)

( * ) Notice: Subject to any disclaimer, the term of this patent is extended or adjusted under 35 U.S.C. 154(b) by 328 days.

(21) Appl. No.: 17/618,977

(22) PCT Filed: Jul. 8, 2019

(86) PCT No.: PCT/IB2019/000804
§ 371 (c)(1),
(2) Date: Dec. 14, 2021

(87) PCT Pub. No.: WO2021/005393
PCT Pub. Date: Jan. 14, 2021

(65) Prior Publication Data
US 2022/0307959 A1   Sep. 29, 2022

(51) Int. Cl.
*G01N 1/22* (2006.01)
*G01N 1/24* (2006.01)
(Continued)

(52) U.S. Cl.
CPC ............ *G01N 7/16* (2013.01); *G01N 1/2226* (2013.01); *G01N 1/24* (2013.01); *G01N 33/241* (2013.01); *G01N 2001/247* (2013.01)

(58) Field of Classification Search
CPC .......... G01N 7/16; G01N 1/2226; G01N 1/24; G01N 33/241; G01N 2001/247; G01N 2001/2229; G01N 1/2232
(Continued)

(56) References Cited

U.S. PATENT DOCUMENTS

| 2,296,852 A | * | 9/1942 | Horner | ................. E21B 49/005 73/149 |
| 2,668,437 A | * | 2/1954 | Patch | ..................... G01N 7/00 73/1.61 |

(Continued)

FOREIGN PATENT DOCUMENTS

| FR | 2721838 A1 | * | 1/1996 | ............... B04C 5/04 |
| FR | 2856797 A1 | * | 12/2004 | ......... G01N 33/2823 |

(Continued)

OTHER PUBLICATIONS

International Search Report and Written Opinion of the International Searching Authority for PCT Application No. PCT/IB2019/000749, entitled "Device for Determining a Volume of Liquid in a Fluid Sample," mailed Feb. 17, 2020.

(Continued)

*Primary Examiner* — Robert R Raevis
(74) *Attorney, Agent, or Firm* — Hamilton, Brook, Smith & Reynolds, P.C.

(57) ABSTRACT

The invention relates to a device for determining a volume of gas in a sample contained in a vessel, the device comprising: a frame configured to attach the vessel; a needle having a longitudinal axis, comprising a proximal part and a distal part, the distal part being configured to pierce the vessel and the proximal part comprising a lumen; and an analysis compartment comprising a cell in fluid communication with the lumen of the proximal part of the needle. The invention also relates to a method for determining a volume of gas in a sample contained in a vessel.

19 Claims, 4 Drawing Sheets

(51) Int. Cl.
*G01N 7/16* (2006.01)
*G01N 33/24* (2006.01)

(58) Field of Classification Search
USPC ............ 73/19.01, 19.05, 19.06, 149, 863.84,
73/864.74, 864.81
See application file for complete search history.

(56) References Cited

U.S. PATENT DOCUMENTS

| | | | |
|---|---|---|---|
| 4,270,381 A | * | 6/1981 | Demaray ................. G01N 7/14 346/72 |
| 5,540,087 A | | 7/1996 | Bickert et al. |
| 8,282,565 B2 | | 10/2012 | Mahapatra et al. |
| 2013/0233054 A1 | | 9/2013 | Oliphant et al. |

FOREIGN PATENT DOCUMENTS

| | | | | |
|---|---|---|---|---|
| FR | 2906482 | A1 | | 4/2008 |
| FR | 2909770 | A1 * | 6/2008 | ......... G01N 33/2823 |
| RU | 111294 | U1 * | 12/2011 | |
| WO | WO-2009050530 | A1 * | 4/2009 | ........... G01N 1/2226 |
| WO | 2012025840 | A2 | | 3/2012 |
| WO | 2016028378 | A1 | | 2/2016 |
| WO | WO-2018111945 | A1 * | 6/2018 | ........... E21B 49/005 |
| WO | 2019048899 | A1 | | 3/2019 |

OTHER PUBLICATIONS

Notification of Transmittal of the International Search Report and Written Opinion of the International Searching Authority for PCT Application No. PCT/IB2019/000804, entitled "A Device for Determining a Volume of Gas in a Sample," mailed Jun. 25, 2020.
Landais, P., et al., "Pyrolysis of Organic Matier in Cold-Seal Pressure Autoclaves. Experimental Approach and Applications," Journal of Analytical and Applied Pyrolysis, 16 (1989) 103-115, Elsevier Science Publishers B.V., Amsterdam.
Michels, R. et al., "Understanding of reservoir gas compositions in a natural case using stepwise semi-open artificial maturation," Marine and Petroleum Geology 19 (2002) 589-599.
Kedziora-Koch, K., et al., "Needle-based extraction techniques with protected sorbent as powerful sample preparation tools to gas chromatographie analysis: Trends in application," Journal of Chromatography A, Elsevier, Amsterdam, NL, vol. 1565, Jun. 19, 2018.
Giordano et al., Measured Negative Pressure in Syringes Used for Aspiration Biopsy, Volume and Pressure Relationship, 198-201, 5(2), May 27, 2019.

* cited by examiner

DEVICE FOR DETERMINING A VOLUME OF GAS IN A SAMPLE

This application is the U.S. National Stage of International Application No. PCT/IB2019/000804, filed Jul. 8, 2019, which designates the U.S., published in English. The entire teachings of the above application are incorporated herein by reference.

TECHNICAL FIELD

The present invention relates to a device for determining a volume of gas in a sample. The present invention also relates to a method for determining a volume of gas in a sample, the method being implemented in the above-mentioned device.

TECHNICAL BACKGROUND

During hydrocarbon exploration and drilling, it is necessary to analyze samples of the rock particles brought up in the drilling mud to determine the proportion of organic matter (oil and gas) in the rock. Until now, this has been done by collecting a sample, placing the sample of the rock particles in a vessel (dish, boat or crucible) within a heated electric pyrolysis furnace, passing a suitable inert carrier gas (helium or nitrogen) over the sample, and analyzing the resultant gaseous samples derived at various temperatures from the pyrolysis of the organic matter in the rock. Thus, upon testing successive samples from different drilling levels, the presence of oil or gas can be detected.

Furthermore, for exploration and exploitation purposes, it is also important to be able to explain gas occurrences in the subterranean formation, in order to provide data for the prediction of petroleum genesis.

Therefore, pyrolysis is considered to be a classical investigation technique in the field of petroleum geochemistry.

Moreover, as the hydrocarbon fluids (comprising oil and/or gas) formed during a pyrolysis process are complex fluids containing many different chemical compounds, it is important to be able to quantify and analyze such fluids with accuracy.

Until very recently, the measurement of gas volume was carried out by using a Toepler pump. However, such pump comprises a significant quantity of mercury which may raise a number of security and toxicity issues. Furthermore, this pump has quite a large size which makes transportation difficult.

Document FR 2 906 482 relates to hydrocarbon thermal cracking modeling by individualizing chemical classes of compounds, by defining a cracking reaction scheme, by defining a kinetic scheme, by carrying out pyrolysis experiments and determining kinetic parameters and stoichiometric coefficients.

The publication of P. Landais et al. "*Pyrolysis of organic matter in cold-seal pressure autoclaves. Experimental approach and applications*", 1989 (doi:10.1016/0165-2370 (89)85010-7) comprises a comparison of natural series of type III coals and type II kerogens as well as details about the experimental vessel and the temperature and monitoring systems. Limitations of the technique and necessary improvements are also discussed.

The publication of R. Michels et al. "*Understanding of reservoir gas compositions in a natural case using stepwise semi-open artificial maturation*", 2002 (doi.org/10.1016/ S0264-8172(02)00033-8) describes experiments to assess the artificial maturation of coal using confined pyrolysis. The experiments were conducted in perfectly closed and in semi-open conditions. The free gases recovered were quantified by gas chromatography and the carbon isotopic composition of individual compounds was determined.

There is thus a need for a device for determining a volume of gas in a sample, notably a sample deriving from the pyrolysis of a hydrocarbon-containing rock sample, which makes it possible to ensure an accurate and safe measurement of the volume of the gas, without such device being cumbersome. There is also a need for a device which allows a complete material balance of a pyrolysis process.

SUMMARY OF THE INVENTION

It is a first object of the invention to provide a device for determining a volume of gas in a sample contained in a vessel, the device comprising:
- a frame configured to attach the vessel;
- a needle having a longitudinal axis, comprising a proximal part and a distal part, the distal part being configured to pierce the vessel and the proximal part comprising a lumen; and
- an analysis compartment comprising a cell in fluid communication with the lumen of the proximal part of the needle.

According to some embodiments, the distal part of the needle is tapered.

According to some embodiments, the lumen is in fluid communication with an opening on a peripheral surface of the needle.

According to some embodiments, the lumen does not extend to a distal end of the needle.

According to some embodiments, the device is configured to provide a relative longitudinal movement of the needle and the frame.

According to some embodiments, the needle is fixed and the frame is movable.

According to some embodiments, the device comprises a first actuating member connected to the frame and configured to longitudinally move the frame relative to the needle, preferably by rotating the first actuating member.

According to some embodiments, the device comprises a sheath surrounding at least part of the needle and having a proximal end and a distal end, the device being configured to provide a relative longitudinal movement of the needle and the sheath.

According to some embodiments, the needle is fixed and the sheath is movable.

According to some embodiments, the device comprises a second actuating member connected to the proximal end of the sheath and configured to longitudinally move the sheath, preferably by rotating the second actuating member.

According to some embodiments, the device comprises a seal located at the distal end of the sheath and configured to press against the vessel.

According to some embodiments, the device comprises a piston slidable in the cell and sealing the cell in a gas-tight manner.

According to some embodiments, the cell comprises at least one pressure sensor and/or at least one temperature sensor.

According to some embodiments, the device does not comprise a Toepler pump.

According to some embodiments, the cell is configured to be in fluid communication with at least one analysis apparatus chosen from a gas chromatography apparatus and a mass spectrometer.

According to some embodiments, the vessel is made of metal, preferably gold, and has a wall thickness of 0.1 to 1 mm, preferably from 0.2 to 0.5 mm.

A second object of the invention is to provide a method for determining a volume of gas in a sample contained in a vessel, the method comprising the steps of:
- attaching the vessel to the frame of the device described above;
- piercing the vessel with the needle of the device;
- transferring gas present in the sample from the vessel to the cell of the device;
- determining the compressibility of the gas within the cell.

According to some embodiments, piercing is achieved by longitudinally moving the frame towards the needle.

According to some embodiments, moving the frame towards the needle is carried out by rotating a first actuating member.

According to some embodiments, the device comprises a sheath surrounding at least part of the needle, and the method comprises retracting the sheath proximally upon piercing.

According to some embodiments, the retraction of the sheath is carried out independently from the movement of the frame.

According to some embodiments, retracting the sheath is carried out by rotating a second actuating member.

According to some embodiments, the lumen of the needle is in fluid communication with an opening on a peripheral surface of the needle, and during the step of transferring gas, the opening is located in the vessel.

According to some embodiments, during the step of piercing the vessel and during the step of transferring gas, there is a gas-tight connection between the vessel and the needle.

According to some embodiments, the compressibility of the gas in the cell is determined by measuring the pressure in the cell as a function of the volume of the cell.

According to some embodiments, the volume of the cell is varied by sliding the piston in the cell.

According to some embodiments, the volume of gas in the vessel is calculated based on the compressibility of the gas and known dead volumes within the device.

According to some embodiments, the method further comprises a step of analyzing at least one portion of the gas, preferably in at least one analysis apparatus in fluid communication with the cell of the device, said analysis apparatus being preferably selected from a gas chromatography apparatus and a mass spectrometer.

According to some embodiments, the method further comprises a step of performing pyrolysis of a source rock sample in the vessel, prior to attaching the vessel to the frame.

According to some embodiments, the gas in the sample derives from the pyrolysis of a source rock sample.

According to some embodiments, prior to the step of piercing the vessel with the needle, the pressure of the gas in the vessel is from 1 to 20 bar, and preferably from 2 to 10 bar.

According to some embodiments, the gas comprises hydrocarbon gas and non-hydrocarbon gas.

According to some embodiments, the hydrocarbon gas comprises hydrocarbon compounds having from 1 to 20 carbon atoms.

According to some embodiments, the non-hydrocarbon gas comprises hydrogen sulfide, carbon dioxide, helium and thiols.

The present invention makes it possible to address the need mentioned above. In particular the invention provides for a device for determining a volume of gas in a sample, notably a deriving from the pyrolysis of a hydrocarbon-containing rock sample, which makes it possible to ensure an accurate and safe measurement of the volume of the gas, without such device being cumbersome. The invention also provides a device which allows a complete material balance of a pyrolysis process.

This is achieved by a device comprising a needle and an analysis compartment comprising a cell fluidically connected to the needle. As the needle comprises a proximal part comprising a lumen, the direct transfer of gas from a vessel to the analysis compartment via the needle is possible without the gas being transferred to intermediate chambers or cells, and therefore without a quantity of a gas being lost or contaminated during the transfer. As a result, the measurement of the volume of gas is directly carried out in the analysis compartment. This accurate measurement of the volume of gas in the analysis compartment, even for very small volumes of gas, makes it possible to carry out a complete material balance.

Furthermore, as the device according to the invention does not comprise a Toepler pump and therefore does not make use of mercury, the process is safe and there are no toxicity issues.

Advantageously, the presence of a sheath around the needle, which preferably is movable relative to the needle independently from the frame, makes it possible to transfer the gas from the vessel to the needle and then to the analysis compartment in a gas-tight manner, without any contamination from the external environment.

DESCRIPTION OF EMBODIMENTS

The invention will now be described in more detail without limitation in the following description.

Device for Determining a Volume of Gas in a Sample

The device according to the invention is used to determine a volume of gas in a sample.

Figure 1:
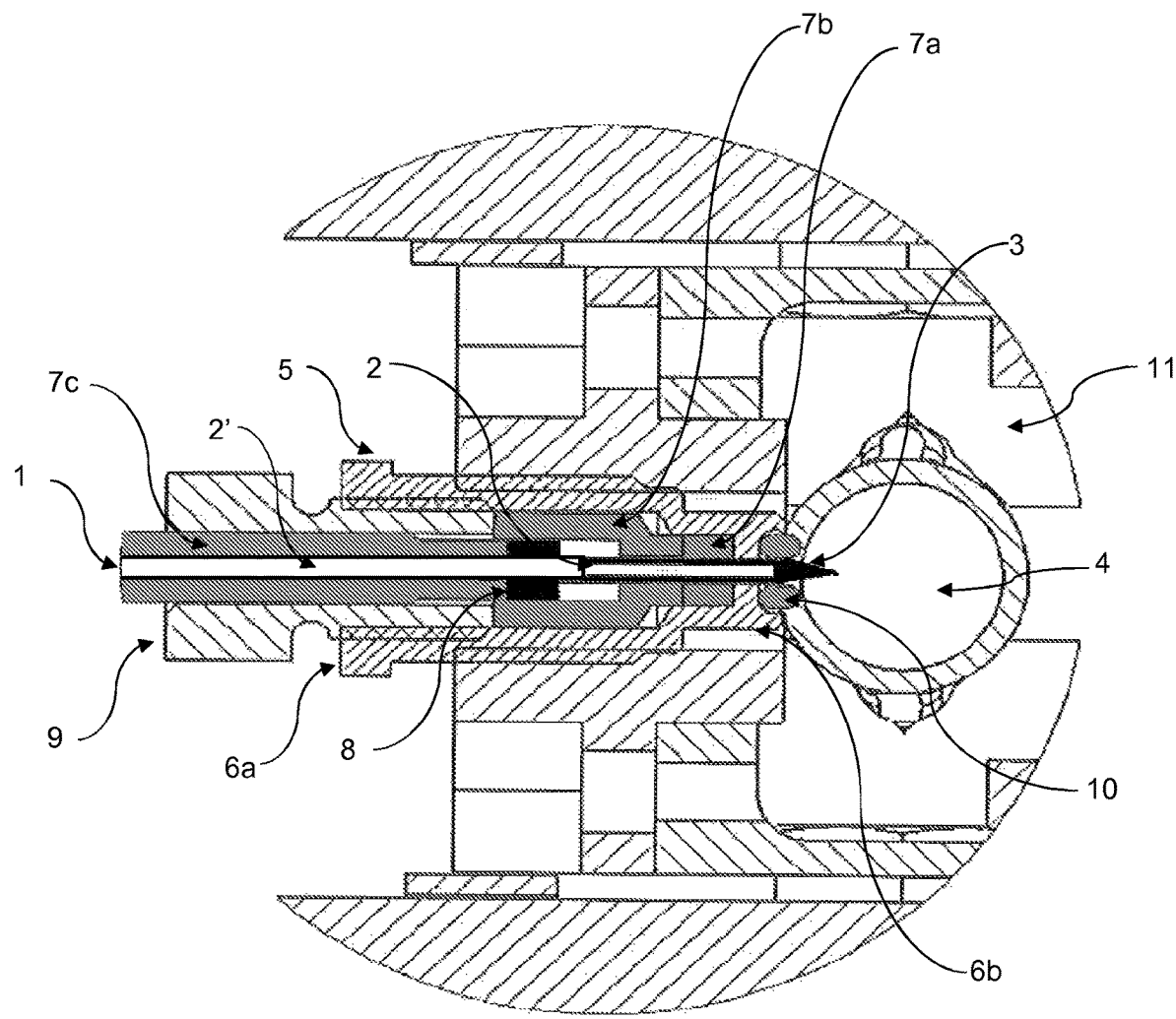
FIG. 1 illustrates a cross-sectional view of the device according to one embodiment of the invention.

Making reference to FIG. 1, the device according to the invention comprises a needle 1 fluidically connected to an analysis compartment and more particularly to a cell comprised in the analysis compartment (not illustrated in the figures). During use, the longitudinal axis of the needle 1 of the device according to the invention is preferably oriented horizontally (parallel to the plane of the horizon), as shown in FIG. 1. The needle 1 is configured to pierce an object such as a vessel (as described in detail bellow) in order to transfer a gas contained in the vessel.

The needle 1 has a longitudinal axis and comprises a proximal part 2 and a distal part 3. By "proximal" is meant a part of the needle that is connected to the analysis compartment. By "distal" is meant a part of the needle that is opposite the proximal part. The distal part 3 of the needle 1 is configured to pierce a vessel 4. The proximal part 2 of the needle 1 comprises a lumen. In other words, the needle 1 is defined by a tubular sidewall, and at least a part of the tubular sidewall is hollow in order to form a tubular channel in the needle 1 (lumen)

By "tubular" is meant a shape of a cylinder with a circular or non-circular base. For example, the base may be a disc, an oval, a square, a rectangle, a regular or non-regular polygon, or a combination of planar surfaces and/or curved surfaces. Preferably, the base is a circular disc.

Preferably, the lumen may extend to the whole length (along the longitudinal axis of the needle 1) of the proximal part 2 of the needle 1.

According to some embodiments, the lumen may also extend to the distal part 3 of the needle 1. This means that the needle 1 is hollow, in other words the lumen may extend on the entire length (along the longitudinal axis) of the needle 1.

According to other, preferred embodiments, the lumen does not extend to the distal end of the needle 1. For example, the lumen may not extend to the distal part 3 of the needle 1. In this case, the interior of the needle 1 is solid (not hollow) at its distal end, and for example in its entire distal part 3. Otherwise, the lumen may extend to only a portion of the distal part 3 of the needle 1.

According to some embodiments, the proximal part 2 of the needle 1 is not tapered, which means that the outer diameter of the proximal part 2 remains constant along the length of the proximal part 2.

The lumen of the needle 1 may have a diameter from 0.05 mm to 0.3 mm, and preferably, from 0.1 mm to 0.2 mm. The diameter of the lumen is the maximum dimension of the lumen in a plane orthogonal to the longitudinal axis.

The proximal part 2 of the needle 1 may have an outer diameter from 0.2 mm to 2 mm and preferably from 0.5 mm to 0.8 mm.

The proximal part 2 may have a length from 0.5 cm to 8 cm and preferably from 0.6 cm to 6 cm.

According to preferred embodiments, the distal part 3 of the needle 1 is tapered, in other words, the outer diameter of the distal part 3 of the needle 1 may decrease gradually along the length of the distal part 3. Therefore, the distal part 3 may have a non-tapered end connected to the proximal part 2 and a tapered end configured to pierce the vessel 4.

The distal part 3 of the needle 1 may have a length from 0.5 mm to 3 mm and preferably from 1 mm to 2 mm.

The needle 1 may comprise an opening 13. This opening 13 is preferably in fluid communication with the lumen of the needle 1.

According to some embodiments and in case the lumen extends to the distal part 3 of the needle 1, the opening 13 may be located on the tapered end of the distal part 3.

Figure 3:
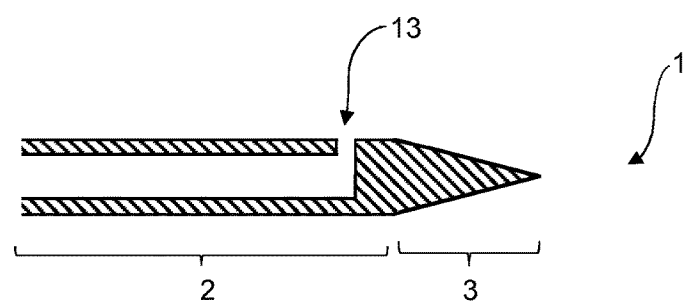
FIG. 3 illustrates a cross-sectional view of part of the needle of the device according to one embodiment of the invention.

According to other, preferred embodiments, notably in case the lumen does not extend to the distal part 3 of the needle 1, the opening 13 may be located on the tubular sidewall of the needle 1, in other words on the peripheral surface of the needle 1, on the proximal part 2, as illustrated on FIG. 3. This embodiment is advantageous as the location of the opening 13 makes it possible to avoid plugging of the opening 13 during the piercing of the vessel 4, for example from the material of the vessel 4. The opening 13 makes it possible to transfer gas from the vessel 4 into the needle 1, as the needle 1 pierces the vessel 4, and the opening 13 is located in the vessel 4.

In some variants, a plurality of openings 13 may be provided instead of one opening 13.

According to some embodiments, the needle 1 is integrally formed as a single piece.

According to other embodiments, the needle 1 is formed by more than one parts assembled together. In this case, it is preferable that the distal part 3 is integrally formed with at least one portion of the proximal part 2. Therefore, as shown in FIG. 1, the needle 1 may comprise for example a first part comprising part of the proximal part 2 and the distal part 3 and a second part, for example a capillary 2' connected to the first part of the needle 1.

The needle 1 may have a length from 0.5 cm to 8 cm and preferably from 1 cm to 6 cm.

The needle 1 may be made from treated steel.

Figure 2:
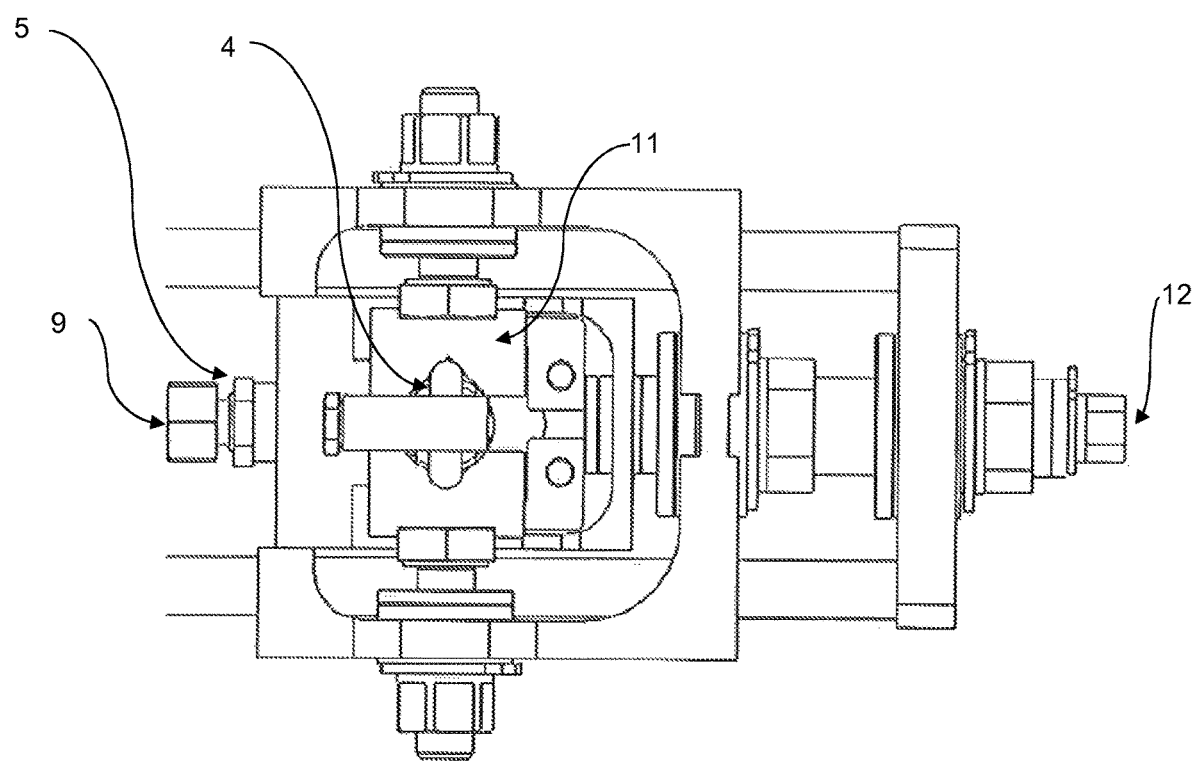
FIG. 2 illustrates a perspective view of the device according to one embodiment of the invention.

As illustrated in FIGS. 1 and 2, the device according to the invention also comprises a frame 11 configured to fix or in other words to attach a vessel 4.

According to some embodiments, the frame 11 may comprise a plurality of gripping elements assembled together to form a grip around the vessel 4 to be attached. This grip makes it possible to block the vessel 4 on the frame 11, by preventing any longitudinal and/or transverse movement of the vessel 4 relative to the frame 11, and by limiting deformation of the vessel 4 upon piercing.

According to other preferred embodiments, the frame 11 may comprise at least four gripping elements, cooperating two by two.

The device may further comprise a first actuating member 12 connected to the frame 11, as illustrated in FIG. 2, opposite the needle 1.

The first actuating member 12 may be configured to provide a relative longitudinal movement of the needle 1 and the frame 11. Actuation of the first actuating member 12 may be manual or automated.

More particularly, the first actuating member 12 may be configured to be rotated in order to move longitudinally the frame 11 towards the needle 1. In other words, the needle 1 may be fixed, while the frame 11 is movable relative to the needle 1.

According to some embodiments, the first actuating member 12 is configured to be rotated relative to the longitudinal axis of the needle 1. This rotation makes it possible to move the frame 11 longitudinally. For example, rotation of the first actuating member 12 in one direction may trigger the movement of the frame 11 longitudinally towards the needle 1 and rotation of the first actuating member 12 in the opposite direction may trigger the movement of the frame 11 longitudinally away from the needle 1.

As illustrated in FIG. 1, a sheath 5 may surround at least part of the needle 1.

The sheath 5 preferably covers at least part of the proximal part 2 of the needle.

Preferably, at least one part of the distal part 3 of the needle 1, and more preferably the tapered end of the distal part 3 of the needle 1 may remain uncovered from the sheath 5. In other words, the sheath 5 may have a proximal end 6a and a distal end 6b and at least part of the needle 1 may be comprised between the proximal and distal ends 6a, 6b while the rest of the needle 1 exceeds these ends 6a, 6b.

According to some embodiments, one or more sealing members 7a, 7b may be present between the needle 1 and the sheath 5 in order to achieve a gas-tight connection between the needle 1 and the sheath 5. Such sealing members 7a, 7b are illustrated in FIG. 1. Such sealing members 7a, 7b may be made from a material chosen from tetra-fluoroethylene (Teflon) or a durable high-performance polyimide-based plastic such as Vespel®.

Furthermore, a connecting part 8 may connect the needle 1 and at least one of the sealing members 7a, 7b (as illustrated in FIG. 1) in order to ensure gas-tightness. The connecting part 8 may be a protruding part on the outer periphery of the needle (1), for example welded to the needle 1.

The connecting part 8 may be made from a material chosen from steel, austenitic nickel-chromium-based superalloys (Inconel), or stainless steel.

The sheath 5 may be made from a material chosen from steel, austenitic nickel-chromium-based superalloys (Inconel), or stainless steel.

The needle 1 and the sheath 5 may be configured to move longitudinally relatively to one another.

Preferably, the sheath 5 may be configured to move longitudinally, relative to the needle 1. By "longitudinally" is meant that the sheath 5 moves along the longitudinal axis of the needle 1.

According to preferred embodiments, the needle 1 is fixed, in other words the needle 1 does not move, while the sheath 5 is movable relative to the needle 1.

Alternatively, the needle 1 may be fixed to the sheath 5.

At its proximal end 6a, the sheath 5 may be connected to a second actuating member 9 as illustrated in FIG. 1. According to some embodiments, and as illustrated in FIG. 1, the second actuating member 9, and preferably at least one part of the second actuating member 9, may be inserted in the sheath 5, for example in threaded engagement. Therefore, the second actuating member 9 may surround at least part of the needle 1, preferably at least part of the proximal part 2 of the needle 1, and the sheath 5 may surround at least part of the second actuating member 9. A gas-tight connection between the needle 1 and the second actuating member 9 may be achieved by at least one sealing member 7c placed between the needle 1 and the second actuating member 9.

The second actuating member 9 may be configured to provide a relative longitudinal movement of the needle 1 and the sheath 5. Actuation of the second actuating member 9 may be manual or automated.

For instance, the second actuating member 9 may be configured to be rotated relative to the longitudinal axis of the needle 1. This rotation makes it possible to move the sheath 5 longitudinally.

At the distal end 6b of the sheath 5, the sheath 5 may comprise a seal 10 that surrounds part of the needle 1, and more particularly part of the distal part 3 of the needle 1. The seal 10 is configured to press against the vessel 4.

The seal 10 may be fabricated from a material chosen from a fluorocarbone rubber, a perfluorinated elastomer, tetra-fluoroethylene (Teflon), a perfluoroelastomer (Kalrez).

According to preferred embodiments, the seal 10 may be an O-ring. When the needle 1 pierces the vessel 4 (as described below), this seal 10 may press against the vessel and thus makes it possible to achieve a gas-tight connection between the needle 1 and the vessel 4, in order to transfer a gas from the vessel 4 to the needle 1 without any loss and without contamination of the gas from the external environment.

The movement of the frame 11 and of the sheath 5 may be independent from each other. For instance, both movements may be performed at a different rate. This makes it possible to ensure a better gas-tight connection between the needle 1 and the vessel 4, as the vessel 4 may deform upon piercing.

As mentioned above, the device according to the invention further comprises an analysis compartment comprising a cell which is fluidically connected to the needle 1, and more particularly fluidically connected to the proximal part 2 of the needle 1.

According to preferred embodiments, the cell of the analysis compartment is directly connected to the proximal part 2 of the needle 1. By "directly connected" is meant that the extremity of the proximal part 2 of the needle 1 is connected to the cell, for example to an inlet of the cell, without the intermediate of tubings or chambers between the needle 1 and the cell.

The cell may be defined by a tubular sidewall.

The cell may comprise at least one inlet, and possibly at least one outlet.

In some embodiments, the cell comprises a single inlet and no outlet. Such a cell can in particular be the chamber of a syringe pump provided with a piston.

Preferably, the cell comprises more than one outlets. For example, the inlet of the cell may be connected to the needle 1, notably to the proximal part 2 of the needle 1, while the outlet of the cell may be connected to a chamber or vessel which makes it possible to discharge the gas contained in the cell. Alternatively and preferably, the outlet of the cell is connected to an analysis apparatus (as will be described below) which allows for the analysis and characterization of the gas comprised in the cell. In this case, the device according to the invention may be in fluid communication with at least one analysis apparatus. In case the cell comprises more than one outlets, each outlet may be connected to a different analysis apparatus, or an outlet may be connected to a discharging vessel while another outlet may be connected to an analysis apparatus.

The cell may have a maximum volume from 0.1 to 30 ml. For example the cell may have a maximum volume from 0.1 to 1 ml; or from 1 to 3 ml; or from 3 to 5 ml; or from 5 to 10 ml; or from 10 to 15 ml; or from 15 to 20 ml; or from 20 to 25 ml; or from or 25 to 30 ml.

The cell is preferably constructed so that it can accommodate an absolute pressure of at least 0.1 bar, more preferably of at least 1 bar. Therefore, the cell can be made of a material such as stainless steel or any other pressure/corrosion-resistant material such as austenitic nickel-chromium-based superalloys (Inconel) or Hastelloy Titanium.

The cell may comprise a piston which is inserted in a slidable manner in the cell. The piston may preferably seal the cell in a gas-tight manner. Therefore, there is no contact between the cell and the external environment. The piston may slide in the cell in order to decrease and/or increase the volume of the cell, and accordingly to increase and/or decrease the pressure in the cell.

The device according to the invention, and more particularly the cell described above, may comprise at least one pressure sensor which can detect the pressure in the cell.

Furthermore, the device according to the invention, and more particularly the cell described above, may comprise at least one temperature sensor (such as thermocouples) which can detect the temperature in the cell.

In addition, the device according to the invention may comprise at least one temperature regulation system, which may comprise a heating and/or a cooling system. For example, use can be made of a refrigerant circuit and/or resistive heating. According to some embodiments, the temperature regulation system may be located in the cell. Alternatively and preferably, the temperature regulation system may be located outside the cell.

Preferably, the device according to the invention does not comprise a Toepler pump. As a result, the device according to the invention is operable without the use of mercury, which allows the operation of the device in a secure and non-toxic way.

Optionally, the device may comprise a purge system for purging the interior of the cell and the interior of the needle 1 from any material present therein.

The device according to the invention may be fluidically connected to at least one analysis apparatus. This makes it possible to directly analyze a quantity of the gas comprised in the cell, without the need of transferring the gas into additional chambers or vessels prior to the analysis. Such analysis apparatus may be chosen from a gas chromatography apparatus and a mass spectrometer.

According to some embodiments, the device is connected to one analysis apparatus.

According to other embodiments, the device is connected to more than one analysis apparatuses. This makes it possible to carry out different analysis of the gas in order to characterize it.

According to some embodiments, the device according to the invention may be part of an assembly. This assembly may comprise for example the device as well as one or more analysis apparatuses as described above. Alternatively, this assembly may comprise the device as well as the vessel 4 comprising the sample. Alternatively, the assembly may comprise the device, the vessel 4 comprising the sample, and one or more analysis apparatuses as described above.

The vessel 4 may be fabricated from a metal, preferably gold.

According to some embodiments, the vessel 4 may have a wall thickness from 0.1 to 1 mm, and preferably from 0.2 to 0.5 mm.

The vessel 4 may be a tube or receptacle, the open extremity or extremities of which have been sealed, e.g. welded. For example, the length of the vessel 4 may be from 5 to 20 cm, and preferably from 6 to 12 cm.

The device of the invention may also comprise—or be associated in a larger system with—an analysis module and/or a control module.

The analysis module may receive data from the pressure and/or temperature sensors, from the monitoring system, from the user and/or from the control module and provide analysis data as an output.

The control module may receive data from the user and/or from the analysis module and may send instructions which make it possible to actuate the piston as well as the various valves of the device. It is possible to operate the device in an automated or semi-automated manner, using appropriate computer hardware and software.

Figure 4:
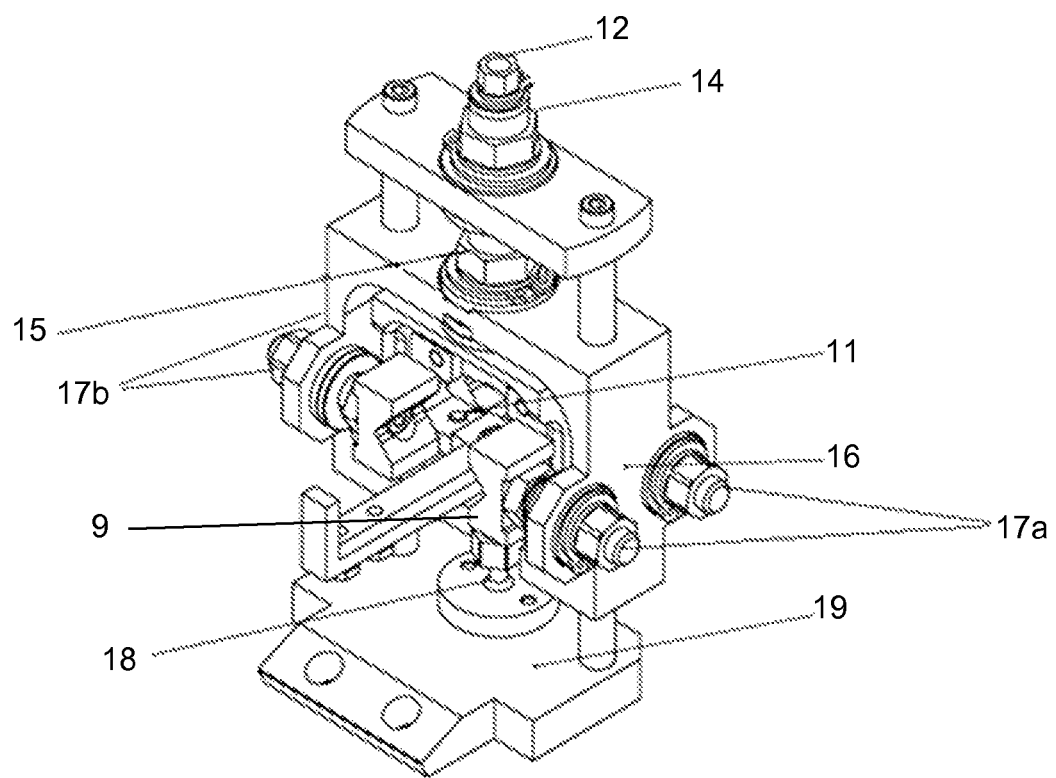
FIG. 4 illustrates a perspective view of a first part of the device according to one embodiment of the invention.
Figure 5:
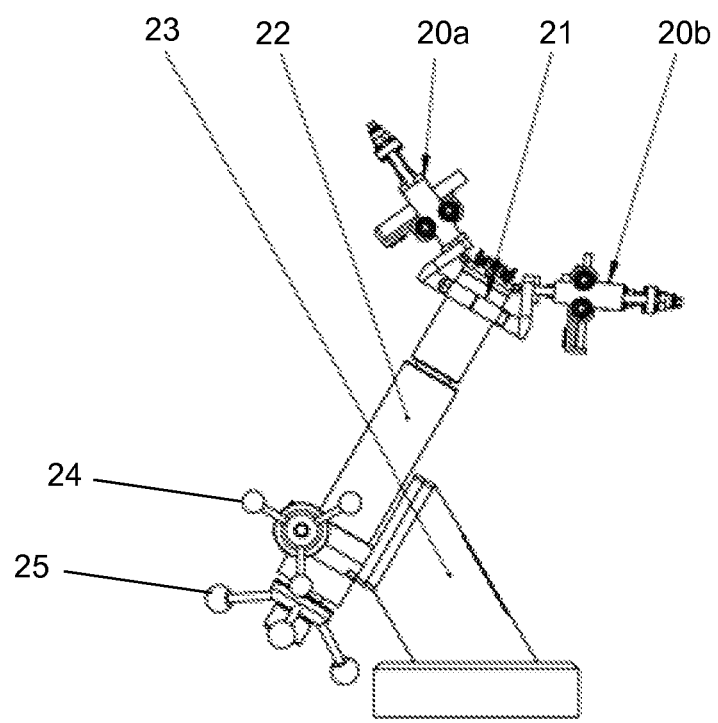
FIG. 5 illustrates a perspective view of a second part of the device according to one embodiment of the invention.

FIG. 4 illustrates a first part of the device according to the invention and FIG. 5 illustrates a second part of the device according to the invention.

FIG. 4 illustrates the frame 11 to which the vessel 4 (not shown) is attached, and the first actuating member 12 connected to the frame 11. It further illustrates a first screwing member 14 connected to the first actuating member 12 and a second screwing member 15. The screwing member 15 may be connected to a mobile support member 16 which supports the frame 11 and the vessel 4 attached to it. The support member 16 may comprise one or more additional screwing members 17a and 17b which make it possible to better place or in other words center the vessel 4 in the frame 11.

FIG. 4 also illustrates the second actuating member 9 which may be connected to the needle 1 as described above.

The second actuating member 9 may be connected to a protection member 18 which makes it possible to "protect" in other words immobilize the needle 1 in case the device according to the invention is not in use.

Furthermore, the support member 16 may be supported on a pedestal system 19.

FIG. 5 illustrates a first piercing member 20a and a second piercing member 20b, both piercing members comprising a needle 1 as described above. Depending on the size of the vessel 4 the first piercing member 20a or the second piercing member 20b may be used. The device illustrated in FIG. 5 further comprises a valve member 21 which makes possible the connection of the device with an analysis apparatus, a control module and/or an analysis module as described above.

In addition, FIG. 5 illustrates a syringe pump 22 which may be connected to the first piercing member 20a and/or the second piercing member 20b, as well as a support system 23 for the syringe pump 22. A gear reducer 24 is associated with the syringe pump 22. A Vernier scale 25 may also be associated with the syringe pump 22, in order to assist with the determination of the volume of the cell.

Method for Determining a Volume of Gas in a Sample

The invention further provides a method for determining a volume of gas in a sample. This method is implemented in the device described above.

The sample preferably comprises a complex fluid comprising various hydrocarbon and non-hydrocarbon compounds. The sample may preferably derive from the pyrolysis of a source rock sample. By "source rock" is meant a rock rich in organic matter which, if heated sufficiently, will generate oil and/or gas.

Source rocks can be recovered from a subterranean formation.

By "pyrolysis" is meant the thermal decomposition of organic matter at elevated temperature in an inert atmosphere. Therefore, during a pyrolysis step, the source rock is processed to release hydrocarbon compounds, which are decomposed. The resulting sample may comprise a liquid fraction and a gaseous fraction.

The liquid fraction may comprise hydrocarbon compounds having from 1 to 350 carbon atoms.

The gaseous fraction (gas) may comprise hydrocarbon gas and non-hydrocarbon gas. The hydrocarbon gas may comprise hydrocarbon compounds having from 1 to 20 carbon atoms. The non-hydrocarbon gas may comprise hydrogen sulfide, carbon dioxide, helium and thiols such as methanethiol, ethylthiol, phenylthiol . . . .

The pyrolysis step may be carried out in the vessel 4 described above. The pyrolysis step may involve heating the vessel 4 to a temperature from 300 to 600° C., during a time period from 3 hours to 3 months. The vessel 4 may be cooled prior to piercing the vessel 4 for a time period of 1 minute for example, into a cool water bath.

The method according to the invention may thus comprise the pyrolysis step.

The method then comprises a step of attaching the vessel 4 on the frame 11 of the device described above.

The method further comprises a step of piercing the vessel 4 comprising the sample with the needle 1 described above, and more particularly with the distal part 3 of the needle 1.

Prior to piercing the vessel 4, the sheath 5 is preferably positioned so that its distal end 6b, or more precisely the seal 10 if present, presses against the vessel 4 and achieves a gas-tight connection of the vessel 4 with the needle 1 when the vessel 4 contacts the needle 1. The method may thus comprise a preliminary step of moving the sheath 5 (e.g.

distally) to properly position it relative to the needle 1. This may be achieved by actuating (e.g. rotating) the second actuating member 9.

Piercing may be achieved by moving the frame 11 (and therefore the vessel 4) and the needle 1 closer together. Preferably, the needle 1 is fixed and the frame is moved towards the needle 1. This may be achieved by actuating (e.g. rotating) the first actuating member 12.

Upon piercing, the vessel 4 may be deformed. In order to maintain a gas-tight connection between the needle 1 and the vessel 4 despite said deformation, the sheath 5 may move longitudinally, e.g. be retracted proximally, independently from the relative movement of the frame 11 and needle 1.

Prior to piercing the vessel 4, the pressure of the gas in the vessel 4 may be from 1 to 20 bar, and preferably from 2 to 10 bar. For example, this pressure may be from 1 to 2 bar; or from 2 to 4 bar; or from 4 to 6 bar; or from 6 to 8 bar; or from 8 to 10 bar; or from 10 to 12 bar; or from 12 to 14 bar; or from 14 to 16 bar; or from 16 to 18 bar; or from 18 to 20 bar.

Once the vessel 4 has been pierced, at least one opening 13 communicating with the lumen is located in the vessel 4. This makes it possible to transfer the gas comprised in the vessel 4 from the opening 13 into the needle 1.

Thus, the method comprises a step of transferring the gas present in the vessel 4 into the cell of the analysis compartment via the needle 1.

The initial pressure in the cell (prior to the transfer of gas) is lower than the pressure in the vessel 4. Preferably, the cell is at atmospheric pressure prior to the transfer of the gas.

As the gas is transferred to the cell through the needle 1 and due to the suppression of the gas in the vessel 4 prior to the piercing of the vessel 4, the pressure in the cell increases. After transfer of the gas to the cell, the pressure in the cell may be from 1 to 20 bar, and preferably from 0.5 to 10 bar.

The method further comprises a step of determining the compressibility of the gas within the cell. The compressibility of the gas in the cell may be determined by measuring the pressure in the cell as a function of the volume of the cell. Thus, the volume of the cell may be varied for example by sliding the piston in the cell. The volume of the cell may be determined automatically, especially in case the sliding of the piston is automated. It may be determined using a displacement sensor. Or it may be determined visually (e.g. using a Vernier scale), especially if the piston is manually actuated. The volume of gas in the vessel 4 may then be calculated based on the compressibility of the gas and the known volume of the cell and known dead volumes within the device, for example the dead volume corresponding to the volume of the lumen of the needle 1.

As the gas is transferred directly from the vessel 4 to the cell, without any contamination or gas loss, the method according to the invention makes it possible to measure the volume of gas in the cell in an accurate manner, even for small volumes of gas. This also allows to carry out a complete material balance of the pyrolysis process.

According to some embodiments, the gas may then be stored in the cell.

According to other embodiments, the gas may then be discharged from the cell for example via an outlet of the cell.

According to other embodiments, after the volume of gas has been determined, the method according to the invention may further comprise a step of carrying out one or more than one analyses of the gas in order to identify for example the components and the composition of the gas. To this end, at least a portion of the gas stored in the cell may be transferred into an analysis apparatus which is connected to the cell via for example an outlet of the cell. Therefore, prior to the analysis, the gas does not come into contact with the external environment, so as to avoid any possible contamination.

According to some embodiments, only one analysis is carried out, therefore an amount of gas is transferred from the cell into an analysis apparatus.

According to other embodiments, more than one analyses may be carried out, therefore different samples (corresponding for example to the number of analyses carried out) can be transferred from the cell into each analysis apparatus.

Such analyses may for example comprise a gas chromatography analysis, a mass spectrometry analysis.

Therefore, as the cell is connected to one or more analysis apparatuses, the method according to the invention makes it possible to analyze and characterize the gas, without additional transfer of the gas prior to its analysis, which makes it possible to limit the analysis time as well as to limit any possible contamination or leaking issues.

Finally, the liquid and solid fraction contained in the vessel 4 may be collected by opening the vessel 4, and be analyzed separately.

The invention claimed is:

1. A device for determining a volume of gas in a sample contained in a vessel (4), the device comprising:
   a frame (11) configured to attach the vessel (4);
   a needle (1) having a longitudinal axis, comprising a proximal part (2) defined as a part of the needle connected to an analysis compartment and a distal part (3) defined as a part of the needle opposite the proximal part, the distal part (3) being configured to pierce the vessel (4) and the proximal part (2) comprising a lumen; and
   the analysis compartment comprising a cell in fluid communication with the lumen of the proximal part (2) of the needle (1), and a piston slidable in the cell and sealing the cell in a gas-tight manner.

2. The device according to claim 1, wherein the distal part (3) of the needle (1) is tapered.

3. The device according to claim 1, wherein at least one of: the lumen is in fluid communication with an opening (13) on a peripheral surface of the needle (1) and the lumen does not extend to a distal end of the needle (1).

4. The device according to claim 1, wherein the device is configured to provide a relative longitudinal movement of the needle (1) and the frame (11).

5. The device according to claim 1, comprising an actuating member (12) connected to the frame (11) and configured to longitudinally move the frame (11) relative to the needle (1).

6. The device according to claim 1, comprising a sheath (5) surrounding at least part of the needle (1) and having a proximal end (6a) and a distal end (6b), the device being configured to provide a relative longitudinal movement of the needle (1) and the sheath (5).

7. The device according to claim 6, comprising an actuating member (9) connected to the proximal end (6a) of the sheath (5) and configured to longitudinally move the sheath (5).

8. The device according to claim 6, comprising a seal (10) located at the distal end (6b) of the sheath (5) and configured to press against the vessel (4).

9. The device according to claim 1, wherein at least one of: (i) the cell comprises at least one of a pressure sensor and a temperature sensor, and (ii) the device does not comprise a Toepler pump.

10. A method for determining a volume of gas in a sample contained in a vessel (4), the method comprising the steps of:
- attaching the vessel (4) to a frame (11) of a device, the device having:
  - the frame (11) configured to attach the vessel (4);
  - a needle (1) having a longitudinal axis, comprising a proximal part (2) defined as a part of the needle connected to an analysis compartment and a distal part (3) defined as a part of the needle opposite the proximal part, the distal part (3) being configured to pierce the vessel (4) and the proximal part (2) comprising a lumen; and
  - the analysis compartment comprising a cell in fluid communication with the lumen of the proximal part (2) of the needle (1);
- piercing the vessel (4) with the needle (1) of the device;
- transferring gas present in the sample from the vessel (4) to the cell of the device; and
- determining compressibility of the gas within the cell.

11. The method according to claim 10, wherein at least one of: piercing is achieved by longitudinally moving the frame (11) towards the needle (1), and moving the frame (11) towards the needle (1) is carried out by rotating an actuating member (12).

12. The method according to claim 10, wherein the device comprises a sheath (5) surrounding at least part of the needle (1), and the method comprises retracting the sheath (5) proximally upon piercing.

13. The method according to claim 12, wherein retracting the sheath (5) is carried out by rotating an actuating member (9).

14. The method according to claim 10, wherein the lumen of the needle (1) is in fluid communication with an opening (13) on a peripheral surface of the needle (1), and during the step of transferring gas, the opening (13) is located in the vessel (4).

15. The method according to claim 10, wherein during the step of piercing the vessel (4) and during the step of transferring gas, there is a gas-tight connection between the vessel (4) and the needle (1).

16. The method according to claim 10, wherein the compressibility of the gas in the cell is determined by measuring pressure in the cell as a function of volume of the cell.

17. The method according to claim 10, wherein the volume of gas in the vessel (4) is calculated based on the compressibility of the gas and known dead volumes within the device.

18. The method according to claim 10, further comprising a step of performing pyrolysis of a source rock sample in the vessel (4), prior to attaching the vessel (4) to the frame (11).

19. The method according to claim 10, wherein the gas in the sample derives from pyrolysis of a source rock sample.

* * * * *